United States Patent
Nell et al.

(10) Patent No.: US 10,315,185 B2
(45) Date of Patent: Jun. 11, 2019

(54) POLYFUNCTIONAL SORBENT MATERIALS

(71) Applicants: University of Oregon, Eugene, OR (US); Battelle Memorial Institute, Richland, WA (US)

(72) Inventors: Kara Nell, Eugene, OR (US); Darren W. Johnson, Eugene, OR (US); Jonathan Pittman, Richland, WA (US); Wilaiwan Chouyyok, Richland, WA (US); Raymond Shane Addleman, Richland, WA (US); Marvin G. Warner, Richland, WA (US)

(73) Assignees: University of Oregon, Eugene, OR (US); Battelle Memorial Institute, Richland, WA (US)

( * ) Notice: Subject to any disclaimer, the term of this patent is extended or adjusted under 35 U.S.C. 154(b) by 0 days.

(21) Appl. No.: 15/650,234

(22) Filed: Jul. 14, 2017

(65) Prior Publication Data

US 2018/0015442 A1 Jan. 18, 2018

Related U.S. Application Data

(60) Provisional application No. 62/362,510, filed on Jul. 14, 2016.

(51) Int. Cl.
*C07F 9/38* (2006.01)
*B01J 20/10* (2006.01)
*B01J 20/30* (2006.01)
*C07C 323/25* (2006.01)
*C07C 323/29* (2006.01)

(52) U.S. Cl.
CPC ......... *B01J 20/3042* (2013.01); *B01J 20/103* (2013.01); *C07C 323/25* (2013.01); *C07C 323/29* (2013.01); *C07F 9/3839* (2013.01); *C07F 9/3847* (2013.01);
(Continued)

(58) Field of Classification Search
CPC .............. B01J 20/3042; B01J 20/103; B01J 2219/00596; C07C 323/25; C07C 323/29; C07F 9/3847; C07F 9/3839; C07F 9/3865; C07B 2200/11
See application file for complete search history.

(56) References Cited

U.S. PATENT DOCUMENTS 5,789,578 A * 8/1998 Burton ............... B01J 20/289
536/112
6,326,326 B1 12/2001 Feng et al.
(Continued)

OTHER PUBLICATIONS

Chouyyok et al., "Surface functionalized nanostructured ceramic sorbents for the effective collection and recovery of uranium from seawater," *Dalton Transactions*, 45(28): 11312-11325, May 2, 2016.
(Continued)

*Primary Examiner* — Anthony J Zimmer
(74) *Attorney, Agent, or Firm* — Klarquist Sparkman, LLP

(57) ABSTRACT

Disclosed herein is a material comprising a functionalized solid support surface, wherein the functionalization comprises a thioalkylene linker bound to the support surface and the thioalkylene linker is coupled to a moiety derived from a ligand, wherein the ligand includes a terminal alkenyl and at least one first functional group configured to bind to at least one predetermined target species.

20 Claims, 12 Drawing Sheets

(52) U.S. Cl.
CPC ... *C07F 9/3865* (2013.01); *B01J 2219/00596* (2013.01); *C07B 2200/11* (2013.01)

(56) References Cited

U.S. PATENT DOCUMENTS

| | | | |
|---|---|---|---|
| 6,846,554 B2 | 1/2005 | Fryxell et al. | |
| 2003/0032043 A1* | 2/2003 | Pohl | B01J 19/0046 506/39 |
| 2013/0095999 A1* | 4/2013 | Chaikittisilp | B01J 20/3278 502/402 |

OTHER PUBLICATIONS

Nell, *Functionalized Nanostructured Silicas for Trace Collection from Natural Waters*, Ph.D. Dissertation submitted to University of Oregon, Sep. 2016.
Rutledge et al., "Thiol-Ene Induced Diphosphonic Acid Functionalization of Superparamagnetic Iron Oxide Nanoparticles," *Langmuir*, 26(14): 12285-12292, Jun. 15, 2010.

\* cited by examiner

| material | surface area (m²/g) | pore size (nm) | chelating ligands/nm² | % thiols reacted |
|---|---|---|---|---|
| MCM-41 | 870 | 3-5 | 0.2 | 8 |
| ball milled MCM-41 | N/A | <5 | 0.4 | 20 |
| davisil 646 | 475-560 | 15 | 0.4 | 21 |
| cab-o-sil* | 380 | NA | 2.0 | 66 |

*5-50 nm particles

POLYFUNCTIONAL SORBENT MATERIALS

CROSS-REFERENCE TO RELATED APPLICATIONS

This application claims the benefit of U.S. Provisional Appl. No. 62/362,510, filed Jul. 14, 2016, which is incorporated herein by reference in its entirety.

ACKNOWLEDGEMENT OF GOVERNMENT SUPPORT

This invention was made with government support under Grant number DE-AC05-76RL01830 awarded by the U.S. Department of Energy. The government has certain rights in the invention.

BACKGROUND

The demand for clean drinking water continues to surge, resulting in an increasing demand for materials and strategies for remediation of contaminated aqueous systems. Clean drinking water is a health concern for the entire population, and as such, is a focal point for the World Health Organization (WHO). Sorbent technologies, like functionalized silica substrates, are prime candidates for water remediation and analytical separations due to their ability to selectively remove harmful contaminants at trace levels. These materials also hold promise for uranium mining from seawater, collection of desired metals from mining streams, and trace collection of specific contaminants in industrial aqueous waste streams. The growth in research in mesoporous silicas and the breadth of application of these materials have expanded greatly over the last twenty years. Functionalized silicas are also applicable in fields such as biomedical engineering, supported catalysis, and molecular motors. The high specific surface area, absorption capacity, robust nature, and tunability of the surface chemistry make functionalized silica substrates particularly well suited as sorbents. Many of these properties are governed by the substrate, but the affinity of the material for a target analyte is dependent on the ligand used for functionalization.

A material's surface dictates the way in which it interacts with its surroundings. The effectiveness of sorbent materials to remove trace organic and inorganic contaminants is dependent upon the ability to install high affinity chelating ligands with high density coverage. The greater the selectivity that the chelating ligand exhibits for the contaminant, the more effective the sorbent will be. To achieve desired affinity and selectivity, it is often necessary to attach somewhat delicate functional groups to material surfaces. Unfortunately, many of the established surface functionalization techniques have suffered from poor ligand loading and attachment with these functional groups. Challenges in the installation of surface chemistries on sorbent supports include long reaction times, steric hindrance from protecting groups, and complete deprotection of the reactive moiety. Steric hindrance leads to a lowered density of ligand loading, while the deprotection and activation of the desired surface chemistry often does not go to completion, further lessening the material's performance. In addition, the deprotection methods commonly used can have detrimental effects on the support materials.

Rare earth elements (REEs) are used extensively in a variety of modern technologies including electronic devices, permanent magnets, automobile catalysts, metallurgical additives, and glass/ceramic additives and polishing. The REEs are extensively produced and purified in three countries: China, USA, and India—with over 80% of world's REE resources presently coming from the mining in China. Due to their importance, the supply of REEs has received increasing attention during this decade, especially for clean energy applications and electronic devices, such as smart phones and computers. This has fueled research and development to improve the collection and recycling of REEs through different techniques from various resources, including natural waters, geothermal fluids, and waste streams of electronic and nuclear wastes. The natural waters (ground, river and sea waters) have been found to contain trace amount of REEs, which are reported to have come partly from mining drainages and waste discharges. While geothermal fluids naturally contain dissolved REEs, their concentration and presence depends on location, source rocks, and temperature.

However, in practice, the recovery and recycling of REEs and precious metals from aqueous resources are still very challenging. This is due to the very low levels of these metals contained in natural waters, geothermal fluids, and waste waters, coupled with the limitations of collection and separation technology. These reasons, combined with the economic demand and recent REE price, show that improved technology for recovery and recycling are needed in the near future.

Solid phase sorption is one of the most extensive and effective techniques for the removal of trace metals from aqueous solutions. It offers a number of advantages, such as flexible configurations, easy application and operation, low waste generation, and the ability to be scaled up and regenerated, resulting in a potential economical solution to REE recycling. The sorption efficiency is dependent on surface area, surface chemistry, and active site density of the sorbent. Functionalized sorbents can be designed, tailored, and synthesized with selected attractive surface chemistries for enhancing the sorption of the trace metals of interests. Several typical sorbents with differing surface chemistries have been developed and applied for REE sorption including metal oxides, ion exchange, chelating and functional group complexation. Among these, the phosphonic acid moieties are the most frequently studied.

Recovering REEs from natural waters using sorbents becomes more economically feasible as the rate of collection, and the concentration of dissolved desired metals increases. The rate of collection is dependent on the concentration of dissolved REEs, the selectivity and affinity of the sorbent, and the water flow rate. There are trace concentrations of dissolved REEs in natural waters, but in geothermal waters and mining discharges the concentrations have been found to be significantly increased. The sorbent materials need to remove the maximum possible amount of REEs, and ideally would be selective to avoid flooding the materials with unwanted species

SUMMARY

Disclosed herein is a material comprising a functionalized solid support surface, wherein the functionalization comprises a thioalkylene linker bound to the support surface and the thioalkylene linker is coupled to a moiety derived from a ligand, wherein the ligand includes a terminal alkenyl and at least one first functional group configured to bind to at least one predetermined target species.

Also disclosed herein is a material comprising:

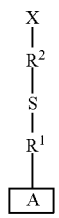

wherein A is a solid support surface; $R^1$ is $(-CH_2-)_n$; $R^2$ is $(-CH_2-)_m$ or $(-CH_2-)_a Ph(-CH_2-)_b$; X is a first functional group configured to bind to at least one predetermined target species; and n is 1 to 6; m is 2 to 6; a is 2 to 6; and b is 1 to 6; wherein Ph is a phenylene.

The foregoing will become more apparent from the following detailed description, which proceeds with reference to the accompanying figures.

DETAILED DESCRIPTION

Disclosed herein are functionalized nanostructured sorbent materials prepared via thiol-ene click functionalization for use in trace collection from water. Thiol-ene click chemistry is an approach to install novel polyfunctional surface chemistry on nanostructured sorbent support to create high performance solid phase extraction materials.

Figure 1:
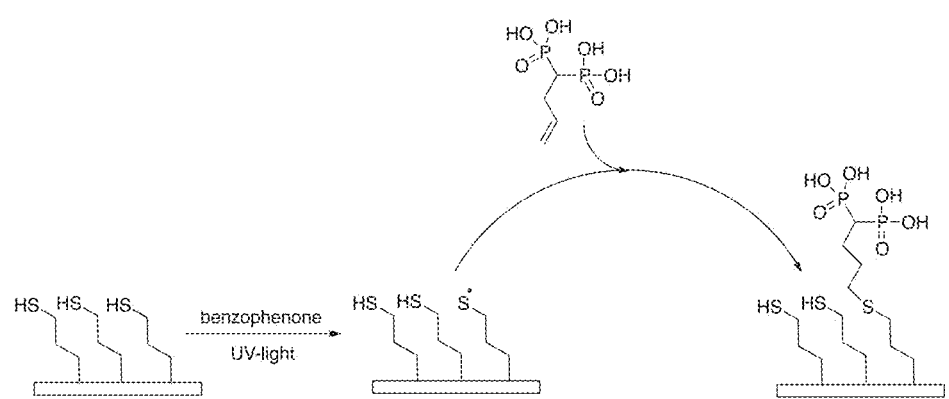
FIG. 1. Scheme for thiol-ene surface functionalization. The silica surface is denoted with a box, this represents any of the silica materials functionalized with mercaptopropyl groups. The DiPhos allyl ligand is shown for illustrative purposes, compounds 2 or 3 also react similarly. All ligands were reacted with the thiol surface in an identical manner—with solvent varying based on ligand solubility.
Figure 2:
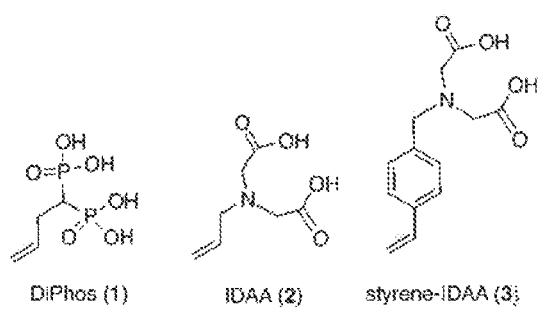
FIG. 2. Ligands used in this study for the thiol-ene click functionalization. The terminal alkene allows for the reaction to occur. The styrene derivative of IDAA had a positive impact on the kinetics ligand loading for functionalization.

The thiol-ene reaction is a UV-promoted click reaction: a rapid method for coupling a thiol to an olefin (FIG. 1). We envisioned the viability of the thiol-ene click would allow for high density installation of reactive chelating ligands without the use of sterically bulky protecting groups, avoiding the need for surface deprotection. More specifically, application of the thiol-ene click process would produce high affinity sorbents using ligands such as diphosphonic acid (DiPhos) and an EDTA analog, iminodiacetic acid (IDAA), which are known to be challenging ligands to attach onto a surface (FIG. 2). First, mercaptopropyl groups can be easily installed on a range of surfaces to serve as a platform for the thiol-ene reaction. The installation of mercaptopropyl functional groups has been previously optimized, and the resulting materials utilized for their soft metal capture capabilities. After thiol surface functionalization, a chelating ligand can be installed by a thiol-ene click reaction. The alkene on the chelating ligand preferentially reacts with the surface thiol, alleviating the need for cumbersome protecting groups while still increasing the potential loading density, and providing a surface where the active sites maintain the correct orientation for metal binding. After adding these chelating ligands to the solid support, the remaining unreacted thiols serve as an additional high affinity surface for softer metals, such as Hg, Ag, and Pb. This, in conjunction with the presence of a DiPhos (IDAA or styrene-IDAA) ligand—which appeal to harder metals (rare earth and actinides)—ensures that the materials have high chemical capture abilities for a wide range of metals in solution. We also demonstrate the advantages of aryl linkage groups between the complexing site and surface by looking at styrene derivatives of the IDAA ligand (styrene-IDAA). (FIG. 2). The sorbent materials were tested for efficacy against a selected set of metals with environmental and industrial relevance, and material performance was shown to be superior to commercially available sorbent products.

Illustrative Support or Substrate Materials

The support or substrate materials are typically solid materials that can be functionalized by covalently attaching a thioalkyl to a surface of the substrate material. Suitable substrate materials include metals, polymers, metal oxides (e.g., silica, alumina, or titania), and nanoparticles (e.g., metal, metal oxide, or semiconductor nanoparticles, such as iron, gold, iron oxide, CdSe, etc.). Typically substrate materials are mesoporous with sufficient strength, porosity, and chemical resistance to be suitable for filtering a fluid and sorbing target species from the fluid.

In certain embodiments, the mesoporous substrate is a silica-based substrate. One example of a silica-based mesoporous substrate material is a molecular sieve with a honeycomb-like porosity, referred to as MCM-41. MCM-41 has hexagonal pores forming channels that can have diameters from 1.5 nm to 20 nm. MCM-41 typically has approximately 80% porosity with typical surface areas from 500 m$^2$ g$^{-1}$ to more than 1000 m$^2$ g$^{-1}$. MCM-41 channel walls are amorphous SiO$_2$. MCM-41 has sufficient structural integrity and chemical resistivity to be suitable for use as a sorbent support material.

Illustrative Target-Binding Groups

The functional group bound to the thioalkylene linker is capable of binding to a target species. In some embodiments, the target species are metals, metalloids, oxyanions, radioactive species, polar organics, and combinations thereof. In particular embodiments, the functional group is —N(CH$_2$CO$_2$H)$_2$, —NHCONH$_2$, —NHCSNH$_2$, —SO$_2$NH$_2$, or —NHCOCH$_2$P(=O)R'R") wherein R' and R" are lower alkyl groups. In certain embodiments, the target species is a metal cation, such as a heavy metal cation (e.g., arsenic, selenium, cobalt, silver, cadmium, mercury, thallium or lead), and the sorbent material has a high affinity (e.g., a distribution coefficient of at least 1×10$^4$) for the target species. In some embodiments, the second compound is an aromatic compound.

Other suitable functional groups include hydroxyl, thiol, carboxyl, ketone, thione, aldehyde, amine, amide (including substituted amide, e.g., carbamide, sulfonamide), imide, imine (particularly phosphate-based imine, e.g., phosphinimine), phosphines, and phosphine oxides. For example, functionalized aromatic compounds with utility for sorbing metals include, but are not limited to, ureas, thioureas, phosphinimines, hydroxypyridinoate (HOPO), sulfocatecholamide (CAMS), terephthalimide, carbamoylmethylphosphine oxide (CMPO), phosphine derivatives, phosphine oxide derivatives, sulfonamide derivatives, and ethylenediaminetetraacetic acid (EDTA) derivatives. Functionalized aromatic compounds with utility for sorbing anions include oxygen-based ligands, such as dihydroxybenzenes (e.g., catechol), and N-phenyliminodiacetic acid. Thus, the sorbent material can be functionalized based upon the identity and/or characteristics of the desired target species.

In certain embodiments, the target-binding functional group comprises a phosphonic acid moiety or an iminodiacetic acid moiety.

EXPERIMENTAL

Synthesis, Material Preparation, and Characterization

Chemicals and sorbents were used as received from Sigma Aldrich, Fisher, TCI America, and Gelest. Tetraethyl methylenediphosphonate was synthesized as described in literature. Unless otherwise noted, reactions were performed in oven-dried glassware and under argon atmosphere. NMR data was collected on 300 or 500 MHz Oxford Varian NMR spectrometer. Thermal gravimetric analysis was performed using at TA Instruments Q500 which was calibrated according to the manufacturer's recommendations. TGA experiments were performed as follows: Temperature was ramped at 20° C. per minute, held for 20 minutes at 120° C. to ensure all nanopure water and solvents were removed, and then ramped to 800° C. at 20° C. per minute, and held for 20 minutes. Surface areas were measured using a Quantachrome QuadrasorbSI. All click reactions were done in a Rayonet RPR-200 Chamber reactor using 350 nm lamps.

Commercially available sorbents were procured from a range of vendors. Activated carbon Darco® KB-B was purchased from Sigma Aldrich. GT-74 Ambersep™ was purchased from Supelco. Chelex-100 resin was purchased from Bio-Rad. Diphonix resin was purchased from Eichrom.

Substrate Functionalized with 3-mercaptopropyltrimethoxysilane

In a 500 mL long neck flat bottom flask, 1.5 g of Cabosil EH5 was stirred for 2 hours with 100 mL of toluene and 0.14 mL of deionized water to hydrate the silica surface. Next, 3 mL of 3-mercaptopropyltrimethoxysilane was added, and the flask was heated to reflux for 84 hours. After the reflux, excess water and methanol were distilled off to ensure complete surface coverage. The flask was slowly cooled to room temperature and filtered through a medium fitted glass funnel. The material was washed 3×50 mL isopropanol followed by 50 mL of methanol and dried under vacuum overnight.

Synthesis of tetraethyl but-3-ene-1,1diylbis(phosphonate) (DiPhos) (1)

To a 250 mL 3-neck flask was added 60% w/w sodium hydride in mineral oil (0.6440 g, 0.016 mol). The flask was flushed with argon for 5 minutes and THF (120 mL) was added with stirring. The slurry was cooled in a dry ice/methanol bath for 15 minutes before tetraethyl methylenediphosphonate (10 mL, 0.040 mol) was slowly added dropwise and then stirred for 1 hour. After stirring, allyl iodide (1.20 mL, 0.013 mol) was added dropwise. The cooling bath was left to slowly warm to room temperature, and the reaction stirred for 24 hours. After the reaction was complete, 50 mL 1 M HCl was added to the reaction and the organic layer was extracted with 100 mL of ethyl acetate. The organic layer was washed with saturated sodium chloride solution (3×50 mL), dried over sodium sulfate, and the solvent removed using a rotary evaporator. A potassium permanganate solution was used to develop the silica TLC plates, showing the product moving above the starting material. Pure material was collected by column purification using a solvent system of acetone:hexanes (1:1). (9.58 g, 73% yield) The first fraction collected is the double substituted diphos ligand, with two allyl arms. The second fraction off the column is the desired product. NMR analysis is consistent with literature.

Deprotection of Diphos Ester

Complete deprotection of the Diphos ester was accomplished before performing click reactions. DiPhos (0.98 g, 3 mmol) was dissolved in 10 mL of dichloromethane. Bromotrimethylsilane (TMSBr) (4.0 mL, 30 mmol) was added, producing a faint yellow solution, which was then allowed to stir under N$_2$ at room temperature overnight. Methanol (10 mL) was then added causing the yellow solution to turn colorless. This solution was stirred for 4 hours before all solvents were removed by rotary evaporation. The resulting dark brown oil was then vacuum-dried overnight before analysis by NMR. (0.648 g, 98% yield) NMR analysis is consistent with literature.

Synthesis of ester allyl IDAA (2)

In a 1 L three-neck round bottom flask, allyl amine (6.2 mL, 0.08 mol) and triethylamine (24 mL, 0.18 mol) were stirred together in THF (400 mL). Ethyl bromoacetate (20 mL, 0.18 mol) was slowly added by syringe. Within 5 minutes of addition, the reaction mixture turned milky white. The reaction was left to stir at room temperature for 60 hours, followed by reflux for 24 hours. After cooling to room temperature, the reaction was filtered to remove triethylamine hydrobromide. The THF was removed by rotary evaporation and 200 mL of 0.5 M HCl was added. The solution was washed with 3×150 mL ethyl acetate. The combined organic layer was dried over sodium sulfate and the solvent removed using a rotary evaporator. The obtained tan oil was passed through a celite/activated carbon/celite plug with acetone and was found to be pure by NMR. (10.72 g, 26% yield) Synthesis was modified from IDAA-silane synthesis.[28] $^1$H NMR (500 MHz, CDCl$_3$): δ 5.87 (m, 1H), 5.19 (dd, 2H), 4.16 (q, 4H), 3.55 (s, 4H), 3.38 (d, 2H), 1.26 (t, 6H).

Deprotection of allyl IDAA

In a 1 L flask, (2.43 g, 0.011 mol) of allyl IDAA was refluxed with 500 mL of 0.5 M HCl for 20 hours. After cooling to room temperature, solvent was removed using rotary evaporation. The product was recrystallized using methanol/acetone. After two recrystallizations, pure material was obtained. (1.91 g, 87.4% yield). $^1$H NMR (500 MHz, D$_2$O): δ 5.97 (m, 1H), 5.66 (d, 1H), 5.62 (s, 1H), 4.04 (s, 4H), 3.97 (d, 2H).

Synthesis of Styrene IDAA (3)

A 250 mL, three-neck round bottom flask was charged with 4-methylchlorostyrene (4 mL, 0.0282 mol), iminodiacetic acid disodium salt (5.00 g, 0.0282 mol), and 80 mL of a 3:1 mixture of ethanol:water. The solution was brought to reflux, and the solution turned a yellow color over 72 hours. After cooling to room temperature, all volatiles were removed via rotary evaporation. The residue was taken up in 50 mL water and rinsed with 3×50 mL diethyl ether. The water stayed a milky white color. The pH was then adjusted to 3 with 1 M HCl and the aqueous layer was washed with 3×50 mL toluene. A layer consisting of undesired side product formed between toluene and water, and was discarded. Addition of 1 M HCl to the aqueous layer yielded a white precipitate. This material was filtered out and shown to be pure product by NMR. (7.02 g, 39% yield). NMR analysis is consistent with literature.

Click Reaction for Installation of Surface Chemistry

In a typical click reaction, 25 mg Cabosil-SH was sonicated with 5 mL methanol in a 20 mL borosilicate scintillation vial. Then, benzophenone (25 mg, 0.14 mmol) was added and sonicated until it dissolved in solution. Respective allyl material was added (58 mg, 0.27 mmol) diphos or ((100 mg, 0.58 mmol) IDAA ligand) along with 1 mL of DI water. The vial was placed in a 350 nm Rayonet UV reactor, and the material was irradiated for 2 hours with rapid stirring. The particles were washed by centrifuging, pipetting supernatant off and dispersing in methanol; this procedure was performed three times. The particles were then dried in air overnight.

Since styrene-IDAA did not dissolve in methanol, slightly different conditions were used. In these trials, (200 mg, 0.80 mmol) of styrene IDAA was dissolved in 6 mL of DMF. To this solution, 50 mg Cabosil-SH was added, followed by sodium borohydride (10 mg, 0.27 mmol) and the reaction was then sonicated. Then, 50 mg benzophenone was added and the reaction mixture sonicated again. The reaction was irradiated in the same fashion and after the desired reaction time in the 350 nm UV reactor, the particles were washed three times with DMSO to remove excess ligand, followed by three washes with methanol to remove DMSO. Note that care had to be taken while pipetting off the supernatant as the particles easily went back into solution. The particles air-dried overnight.

Material Performance Testing
Batch Contact Sorption Experiments $K_d$ value and capture (%) of metals from natural waters (filtered river water and filtered seawater) and acidic solutions (0.01 M $HNO_3$ and 0.01 M HCl) were obtained through batch contact experiments. The metal ion solutions were prepared from ICP standard solutions, purchased from Aldrich. Metal ions of Eu, Co, Ag, and U were spiked in seawater to study the sorbents under challenging conditions and equilibrium conditions (after spiking from acidic solutions and deprotonation of sorbents) were typically around pH 6.0. Natural waters and acidic solutions were both tested. Typically, ~4.9 mL of the metal solution was placed in a polypropylene bottle and spiked with 0.1 mL sorbent suspended in DI water to obtain a liquid to solid ratio of 50,000 (L/S in mL/g). The tubes were shaken for 2 hours at 200 rpm on an orbital shaker. The solution was then removed by filtering through 0.45-μm syringe Nylon-membrane filters. The filtrate was kept in 2 vol. % $HNO_3$ prior to metal analysis using ICP-MS (ICP-MS, Agilent 7500ce, Agilent Technologies, CA). The metal ion concentration in control experiments (no sorbent) was treated in the same fashion as the test solutions; however, the control without filtration was also analyzed in order to check for precipitation of metal ions. The $K_d$ and % capture measurements were calculated from the actual concentrations of metals detected by ICP-MS. Commercially available sorbents (i.e. Activated carbon KB-B, GT-74, Chelex-100, and Diphonix resin) were used under the same experimental conditions and compared to the new materials synthesized for this study. All batch experiments were performed in triplicate and the averaged values were reported.

Results and Discussion
The Thiol-Ene Click Process

Thiol based sorbent materials have been shown to be excellent sorbents for the capture of soft heavy metals such as mercury, silver, and lead. The functionalization of silica materials with 3-mercaptopropyl ligands has been optimized, reaching near theoretical limits for surface coverage with thiol groups. For the thiol-ene click reaction surface thiols are reacted with a terminal alkene on the chelating ligand. The resulting materials exhibit affinities for soft metals such as gold, due to the thiol, and harder metals such as uranium, due to the specific chelating ligand. Subsequently, we explored the reaction conditions needed for creation of such materials, the impact of the sorbent support material, and evaluated the performance of preferred materials. A variety of mercaptopropyl functionalized silica substrates, with various loadings on Cab-o-sil, Davisil, and MCM-41, were prepared using previously described methods. The thiol coverage loadings were varied on all substrates, ranging from the theoretical maximum around 3 thiols/$nm^2$ down to 0.5 thiols/$nm^2$. We chose 0.5 thiols/$nm^2$ as our lower limit since we are aiming for high chelating ligand density and to have materials that still have unreacted thiol sites. Thermogravimetric analysis (TGA) was used to determine the organic content of the material and calculate the ligands per surface area. The loading ranged from 0.5 to 3.1 mercaptopropyl groups per $nm^2$. These thiol-functionalized materials were then used as a base for further thiol-ene click functionalization, which resulted in a polyvalent material.

Installation of IDAA Chelating Ligand

The iminodiacetic acid ligands, allyl derivative (2), and styrene derivative (3), were prepared via previously described methods. Once the ligands were in hand, they were dissolved in methanol (2) or DMF (3), respectively. The thiol functionalized substrate was then dispersed in the solution. Benzophenone, a photo-initiator, was added and the reaction was placed in a UV-reactor and underwent irradiation, while stirring, for the allotted time. Then, the material was centrifuged down and the supernate was pipetted off. The materials were washed several times with methanol, as well as dimethylformamide for 3, and dried in a vacuum oven, before TGA analysis. Comparing ligands 2 and 3 provided insight into the impact of having an aryl group in the ligand backbone. It has previously been shown that having an aryl group can help rigidify the molecule, limiting degrees of freedom, as well as pre-organize the ligand during surface attachment: both of these effects are thought to drive high density loading. In fact, it was observed that the styrene derivative (3) did show higher density loadings (Table 1). When observed over a short time span (one to two hours in increments) 3 comes close to reacting to completion with surface thiols, while 2 remains under 50% reacted. This increased ligand density could also be impacted by the stability of the benzyl radical that is formed during this reaction. Materials made with both ligands went on to perform excellently in comparison to commercially available sorbents. So while one may be more ideal kinetically, both ligands provide materials with outstanding performance.

TABLE 1

Time Series for Thiol-ene Ligand Coupling to Surface. Silica substrate used was Cab-o-sil EH-5, a fumed particle silica. The effect of time varied between allyl and styrene IDAA.

| Ligand | Rxn Time (hours) | Thiols/nm$^2$ | Chelating ligands/nm$^2$ | % Thiols reacted |
|---|---|---|---|---|
| Allyl IDAA | 1 | 2.81 | 1.02 | 36 |
| Allyl IDAA | 1.5 | 2.81 | 1.19 | 42 |
| Allyl IDAA | 2 | 2.81 | 1.01 | 36 |
| Styrene IDAA | 1 | 3.06 | 2.24 | 73 |
| Styrene IDAA | 1.5 | 3.06 | 2.73 | 89 |
| Styrene IDAA | 2 | 3.06 | 3.00 | 98 |

The role of a reducing agent, NaBH$_4$, as well as the importance of the photoinitiator were investigated. It was found that the addition of sodium borohydride increased the loading from 0.85 to 3.00 ligands/nm$^2$ for styrene IDAA (3) after two hours. However, it decreased the loading of the allyl IDAA (2) from 1.01 to 0.16 ligands/nm$^2$. The lower loadings with 2 and higher loadings with 3 were consistent over four time points from 1 to 4 hours. Due to the inconsistent effects of sodium borohydride from ligand to ligand, it was not included in future reaction conditions. It has been previously noted in literature that the thiol-ene click reaction does not necessarily require the use of a photoinitiator. We ran the IDAA thiol-ene click reaction with IDAA with and without photoinitiator and found that while there was still some conversion from the thiol to the thioether without the photoinitiator, the loading of IDAA dropped by an order of magnitude. With this knowledge, it was determined that the photoinitiator should be used for future reactions.

Installation of DiPhos Chelating Ligand

The tetraethylmethylene bisphosphinate was synthesized as described in literature, and the alkene functionality was introduced using the same method our group has previously published. Although the reaction was not previously optimized, we achieved high yields by deprotonating the diphosphonate methylene carbon using sodium hydride, followed by alkylation with allyl iodide. The product can be deprotected to afford the free diphosphonic acid, DiPhos, which can then be installed on the surface without protecting groups. DiPhos went on to undergo the same thiol-ene reaction conditions as 2 in the previous section.

3.3.4 Impact of Substrate

Thiol surface chemistry, which enables the thiol-ene click route of functionalization, can be installed on a range of ceramic, metallic, and carbon based supported material. This enables a wide variety of potential support materials to be utilized with the thiol-ene click reactions. For this study, a range of high surface area silica support materials that span from a highly ordered mesoporous silica to a small particle fumed silica (Table 2), were evaluated. These materials all have high surface areas, 380-870 m$^2$/g which allow for a large number of active sites per gram of silica. The thiol loading can vary with substrate, but by comparing the percent of surface thiols reacted, the effectiveness of the thiol-ene click reaction with allyl IDAA on various surfaces was assessed (Table 2).

TABLE 2

Impact of Substrate Material on IDAA Ligand Loading.

| Support Materials | Surface area (m$^2$/g) | Particle size range (um) | Average pore size (nm) | Chelating ligands/nm$^2$ | Thiols/nm$^2$ | % Thiols reacted |
|---|---|---|---|---|---|---|
| Nanoporous Silica$^a$ | 870 | Variable | 3-5 | 0.24 | 2.72 | 8 |
| Porous Column Silica$^b$ | 475-560 | 250-500 | 15 | 0.41 | 1.90 | 21 |
| Nonporous Fine Silica$^c$ | 380 | 0.2-0.3 | N/A | 1.01 | 2.19 | 66 |

Substrates were reacted for 2 hours in methanol under stated click conditions.
$^a$MCM-41 is a mesoporous silica well-ordered uniform pore structure.
$^b$Davisil 646 is a porous silica with less uniformity when compared with MCM-41.
$^c$Cab-o-sil EH-5 is a small particle fumed silica.

When reacting allyl IDAA with a variety of thiol functionalized substrates, it was found that small pore sizes in porous silica were detrimental to the click reaction on the materials surface. It can be observed in Table 1 that nanoporous silica, MCM-41, which has the smallest pores (5.6 nm), showed the poorest ligand loading. A material with larger pores such as Davisil 646 (15.6 nm pores), enables improved loading with the click reaction. Not surprisingly, the most effective ligand loading is on nonporous materials that do not impose mass transport and steric constraints on the reaction fine fumed silica fibers, cab-o-sil; with 66% of the sites modified after a few hours of reaction time. Since Cab-o-sil had superior performance with this reaction, it was used in future reactions; however, the method can be applied to porous materials as well, and can be expanded onto a wide variety of form factors.

Ligands Impact on Loading

All three ligands used, allyl and styrene IDAA and DiPhos were run under the same click reaction condition to explore the ligand type impact on loading density. Comparing all three ligands when reacted with thiol Cab-o-sil (fumed silica base), styrene IDAA (3) and DiPhos (1) exhibited higher ligand density coverage after two hours (Table 3). Given longer reaction times the density of allyl IDAA surface ligands can be driven up to 2 ligands per nm$^2$.

TABLE 3

Impact of chelating ligand structure on loading density. Allyl derivatives reacted in methanol and the styrene ligand required dimethyl formamide to be solvated. Silica substrate used was cab-o-sil, a fumed particle silica. Stated click conditions were used.

| Ligand | Rxn time (hours) | Thiols/nm$^2$ | Chelating ligands/nm$^2$ | % Thiols reacted |
|---|---|---|---|---|
| Allyl IDAA | 2 | 2.81 | 1.01 | 36 |
| Styrene IDAA | 2 | 3.06 | 3.00 | 98 |
| Allyl DiPhos | 2 | 3.06 | 2.73 | 89 |

We attempted making a styrene analog of DiPhos to improve ligand loading. It was thought that the same positive gain in ligand density would be achieved due to preorganization and added rigidity. Unfortunately, styrene DiPhos was found to be so reactive that it gelled when placed in the UV-reactor, before the ligand was able to react with the thiol surface, likely making a homo-polymer.

Impact of Ligand Density on Performance

Figure 3:
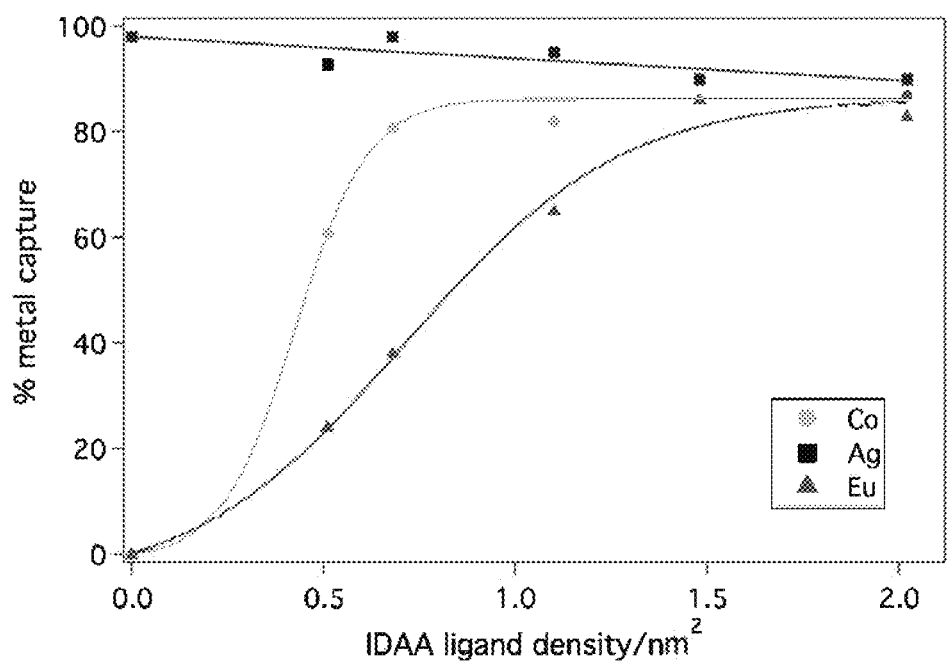
FIG. 3. IDAA Ligand Density Impact on % Capture of Selected Hard, Intermediate and Soft Metals. Lines of best fit are shown to help display trends. Varying trends were observed with all three metals, with ligand density having a significant impact on europium and cobalt. However, the decrease in thiol coverage did not have as large of an impact.

One of the main advantages of using the thiol-ene click reaction for surface functionalization is increased ligand density. Ideally there would be the highest number of chelating ligands on the surface as possible, however the soft surface given by the surface thiols is still desired. In order to see the effect that ligand density truly had on performance, a range of materials with varying densities of allyl IDAA were made, and materials were tested for percent uptake (FIG. 3). The ligand density of IDAA was increased from zero up to two ligands per nm². At zero IDAA ligands, there was the highest thiol ligand coverage, as none of the thiols have undergone the click reaction. At the zero point for IDAA ligand density, we observed almost 100% soft metal, in this case, Ag(I), capture. As the thiol ligand density was decreased and the IDAA ligand density increased to 2 ligands per nm², a slight decrease in soft metal capture is observed. However, this decrease is less than expected and these materials still exhibit excellent soft metal capture. There is a dramatic impact on percent capture of europium when increasing ligand density: increasing the IDAA loading from 0.5 to 2.0 ligands/nm² increased the percent europium (Eu) capture from 25% to ~85%, respectively. The percent capture of cobalt is also improved with higher ligand density. For each element in FIG. 3, lines of best fit were drawn to help guide the eye towards the trends. The significant increase in harder metal capture, while also maintaining excellent soft metal capture, shows that we have successfully made materials with high density of chelating ligands that directly correspond to excellent percent capture capabilities, all while maintaining a polyvalent surface that allows for excellent soft metal capture as well.

Competitive Performance Testing

Functionalizing materials via a thiol-ene click reaction is beneficial for synthetic reasons, but more importantly, it allows the synthesis of materials with outstanding sorbent performance. These new functionalized materials were tested over a range of pH conditions, from acidic to neutral, and in real seawater.

When evaluating material performance, both the percent uptake and distribution coefficient were considered. The initial comparison and evaluation of sorbent materials for metal collection from seawater was conducted using batch contact studies at equilibrium conditions. The sorption affinity of each sorbent is presented in terms of the solid phase distribution coefficient ($K_d$) and/or as the percent (%) capture. The $K_d$ (mL/g) is simply a mass-weighted partition coefficient between supernatant phase and solid phase (Equation 1). For the specific conditions of the experiment, the $K_d$ represents a direct measurement of chemical affinity. For trace collection, the $K_d$ is a key parameter for evaluation of sorbent performance. The percent capture was calculated as shown in Equation 2, where $C_o$ and $C_f$ are the initial and final equilibrium concentrations of desired analyte, respectively, V is the volume of solution, and M is the mass of sorbent used.

$$K_d = \frac{(C_o - C_f)V}{C_f M} \quad (1)$$

$$\% \text{ capture} = \frac{(C_o - C_f)}{C_f} \times 100 \quad (2)$$

A variety of commercially available sorbents, as well as the engineered functionalized silica sorbents, were tested (Table 4). Activated carbon is a prominently utilized sorbent, it underperforms when compared to engineered sorbents, but is very economically feasible. The three resins tested contain the same functional groups as the prepared high surface area silica supports (HSASS). The Chelex 100 resin contains iminodiacetic acid functional groups, Diphonix contains diphosphonic acids, and thiol resin has surface thiol groups. Across the board, the HSASS counterparts outperform commercial sorbents, exhibiting affinities that are, in some cases, multiple orders of magnitude higher than these resins. For example, DiPhos-thiol HSASS outperforms Diphonix by an order of magnitude in uranium affinity, and the percent capture increases from 78% to 96%. Comparing the rare earth metal affinity of these same two materials DiPhos-thiol HSASS has an improvement of two orders of magnitude, and the percent uptake increases from 54% to 99%. All of the HSASS materials maintain the polyvalent surface, which allows for maintaining excellent soft metal uptake. It is clear to see that HSASS materials exhibit outstanding performance, even when compared with their commercially available resin counterparts. Utilizing the thiol-ene click reaction, we have been able to synthesize polyvalent materials with excellent metal sorbent performance.

We have been successful in creating a new class of polyfunctional silica materials by utilizing the thiol-ene click reaction. Thiol based sorbent materials have been shown to be excellent sorbents for the capture of soft heavy metals such as mercury, silver, and lead. Using mercaptopropyl groups as the platform surface, allowed the materials to maintain a high affinity for softer metals, while allowing for facile secondary functionalization through thiol-ene click chemistry. This method allowed for functionalization of the silica substrates with highly active ligands that have otherwise proven to be challenging to incorporate. The use of bulky protecting groups that can negatively impact ligand density was alleviated, along with the necessary harsh deprotection step, allowing for improved ligand density. The thiol-ene click reaction is performed quickly, and in most cases, can be pushed almost to completion. However, it was undesirable to convert all surface thiols, so driving the reaction to completion was not an aim. Increasing loading of the chelating ligands on the materials surface had a

TABLE 4

$K_d$ and Uptake of Selected Commercial and Thiolene Click Sorbents. HSASS stands for high surface area silica support. Initial metal concentration =~ 50 ppb in seawater. L/S = 50,000. pH ~6. Sea water originated from Sequim Bay on Washington coast of the Pacific Ocean.

| Sorbent | Eu Hard Metal[a] | Co Intermediate Metal[a] | Ag Soft Metal[a] | U Actinide |
|---|---|---|---|---|
| Activated Carbon | | | | |
| $K_d$ | $3.1 \times 10^4$ | $6.2 \times 10^3$ | $8.2 \times 10^3$ | $1.3 \times 10^5$ |
| % uptake | 38 | 11 | 14 | 72 |
| HSA Silica Support[e] | | | | |
| $K_d$ | $1.9 \times 10^4$ | $1.3 \times 10^3$ | $9.7 \times 10^2$ | $6.0 \times 10^5$ |
| % uptake | 27 | 3 | 2 | 92 |
| Thiol Resin[b] | | | | |
| $K_d$ | $3.6 \times 10^3$ | $1.9 \times 10^3$ | $4.2 \times 10^4$ | $1.3 \times 10^4$ |
| % uptake | 7 | 4 | 45 | 20 |
| Thiol HSASS | | | | |
| $K_d$ | $6.8 \times 10^3$ | $3.5 \times 10^3$ | $3.3 \times 10^7$ | $5.5 \times 10^4$ |
| % uptake | 12 | 6 | 99 | 52 |
| Chelex 100 Resin[d] | | | | |
| $K_d$ | $1.9 \times 10^4$ | $8.5 \times 10^3$ | $1.6 \times 10^4$ | $4.4 \times 10^4$ |
| % uptake | 27 | 15 | 24 | 47 |

TABLE 4-continued $K_d$ and Uptake of Selected Commercial and Thiolene Click Sorbents. HSASS stands for high surface area silica support. Initial metal concentration =~ 50 ppb in seawater. L/S = 50,000. pH ~6. Sea water originated from Sequim Bay on Washington coast of the Pacific Ocean.

| Sorbent | Eu Hard Metal[a] | Co Intermediate Metal[a] | Ag Soft Metal[a] | U Actinide |
|---|---|---|---|---|
| IDAA-thiol HSASS | | | | |
| $K_d$ | $7.1 \times 10^4$ | $6.3 \times 10^5$ | $2.4 \times 10^6$ | $1.7 \times 10^6$ |
| % uptake | 59 | 92 | 98 | 97 |
| Styrene IDAA HSASS | | | | |
| $K_d$ | $4.3 \times 10^5$ | $8.2 \times 10^5$ | $1.0 \times 10^6$ | $1.1 \times 10^6$ |
| % uptake | 90 | 94 | 95 | 96 |
| Diphosphonic Acid Resin[c] | | | | |
| $K_d$ | $6.0 \times 10^4$ | $6.3 \times 10^3$ | $9.8 \times 10^3$ | $1.8 \times 10^5$ |
| % uptake | 54 | 11 | 16 | 78 |
| DiPhos-thiol HSASS | | | | |
| $K_d$ | $7.5 \times 10^6$ | $2.9 \times 10^3$ | $2.2 \times 10^6$ | $3.5 \times 10^6$ |
| % uptake | 99 | 5 | 98 | 99 |

[a]Hard, intermediate and soft as defined by Pearson.[31]
[b]Dow Ambersep GT74
[c]EiChrome Diphonix resin
[d]BioRad Chelex 100 (EDTA based surface chemistry similar to IDAA)
[e]Cab-o-sil EH-5 large impact on the material's affinity for rare earth elements; however, all polyfunctional materials exhibited excellent affinity for soft metals. Fortunately, although there was a slight decrease as the number of surface thiols decreased 90% soft metal capture is maintained. Since the functionalization of many different types of ceramics and polymeric materials with thiols is so prevalent, this functionalization motif can be used for a variety of nanomaterials, expanding the potential impact.

The applications of these materials span from mining to water purification. Selectively capturing species present in incredibly low concentrations from various aqueous matrixes is challenging. The applications in water purification are driven from the need for clean water: soft heavy metals and radioactive elements are harmful in our water systems, even in parts per billion concentration ranges. Capturing soft metals and rare earths can also be applied to mining streams that may have valuable dissolved metals, as well as for use in mining uranium from seawater. These materials were designed for use in broad chemical spectrum water purification and mineral recovery, and are well suited for collection from challenging solutions, such as mine run off, industrial waste, recycling, and challenging brine solutions. By utilizing the thiol-ene click functionalization motif we were able to assemble materials that outperform commercially available sorbents and hold promise throughout a wide array of applications.

Geothermal waters were an area of focus for ideal dissolved metal concentrations and market accessibility. Geothermal waters from a variety of sites were analyzed for metal concentrations, and while not all locations were ideal, the Salton Sea was identified as a possible area of interest. Dissolved metal concentrations were determined, and an economic analysis on incorporation of desired dissolved metal capture into geothermal plants has also been carried out.

EXPERIMENTAL

Materials

The support materials such as Cab-o-Sil® EH5 (NF silica), Davisil 635 (PC silica), and MCM-41 (NP silica) were obtained from Cabot, Sigma-Aldrich, and ExxonMobil, respectively. Chelex 100 resin were purchased from Biorad. Activated carbon, Darco® KB-B, was obtained from Sigma-Aldrich.

Synthesis and characterization of organic ligand-based nanoporous (NP) silica were as described above, including those functionalized with propionamide phosphonic acid (PropPhos), and iminodiacetic acid (IDAA). Diphosphonic (Diphos) and IDAA were functionalized on nanofiber (NF) silica by "thiol-ene click" reaction, and details were explained above. For comparison, the unfunctionalized (support materials) and commercially available materials were also tested along with functionalized materials. The sorbent characterization (surface area and particle size) are shown in Table 5.

Surface area and pore size data were collected using a Quantachrome QuadrasorbSI. The ligand densities were calculated from mass loss of organic attached sorbent obtained by Thermal Gravimetric Analysis (TGA). The TGA was performed using a NETZSCH TG 209 F3 Tarsus in an aluminum oxide crucible under a helium purge of 10 mL/min. The thermal ramp rate was 10° C./min and points were collected every 0.5° C.

5.2.2 $K_d$ and Percent Sorption Measurements

The $K_d$ is a mass-weighted partition coefficient between solid phase and liquid supernatant phase as shown in Equation 1. The percent sorption of REEs was calculated as shown in Equation 2, where $C_o$ and $C_f$ are the initial and final concentrations of the REE, respectively (at equilibrium), V is the volume of solution, and M is the mass of sorbent used.

$$K_d = \frac{(C_o - C_f)V}{C_f M} \quad (1)$$

$$\% \text{ capture} = \frac{(C_o - C_f)}{C_f} \times 100 \quad (2)$$

$K_d$ and percent sorption of REEs by sorbents were performed in filtered river water (Columbia River, Washington State), filtered seawater (Sequim Bay, Washington State), 0.01 M $HNO_3$, and 0.01 M HCl. They were obtained through batch sorption experiments, and calculated from the actual concentrations of metals detected by ICP-MS. River water was spiked with ~50 ppb of the REEs La, Ce, Nd, Eu, Gd, Tb, Dy, Ho and Lu, and then the pH was adjusted to an initial value of 5.2 with $HNO_3$ to avoid precipitation. 4.9 mL of the REEs river water was placed in a polypropylene bottle and mixed with 0.1 mL sorbent suspended in DI water to obtain a liquid-to-solid (L/S) ratio of 50000 (mL liquid/g-sorbent). The tubes were shaken for 2 h at 200 rpm on an orbital shaker. The materials were collected by filtering the solution thru 0.45-μm syringe Nylon-membrane filters. The removed supernatants were stored in 2% (vol.) aqueous $HNO_3$ prior to metal analysis. The metal ion concentrations in the control (no sorbent), with and without filtration, were analyzed in order to check for precipitation of metal ions and confirm concentrations. The same batch contact conditions were used for the seawater. The initial pH of the REEs spiked seawater was also adjusted to be ~5.2, while the REEs spiked solutions in 0.01 M $HNO_3$ and 0.01 M HCl were retained with pH as is (~pH 2.2). These sample solutions were analyzed using an inductively coupled plasma mass spectrometer (ICP-MS, Agilent 7500ce, Agilent Technologies, CA). All batch experiments were performed in triplicate and the averaged values were reported.

Sorption Kinetics

Europium was selected as a representative REE, due to its mid-range weight, for sorption kinetics of selected materials. The sorption kinetics were carried out in seawater under the same condition as batch contact studies (equilibrium pH ~6.0 and L/S ratio of 50000 mL/g), except that the sample volume was increased to 50 mL to minimize the change in L/S ratio due to the frequent samplings. A well-mixed 1 mL aliquot sample was taken at selected times from 0 min through 24 hours the liquid was separated from the sorbent via filtration and stored in 2% $HNO_3$.

Sorption Capacity

The sorption capacity of sorbents for REEs was measured with the same method and conditions employed for the $K_d$ measurements. Europium was selected to represent the sorption capacity of sorbents in river water. The initial Eu concentration was varied until the maximum sorption capacity was obtained. The batch contact was carried until equilibrium was reached. This was accomplished by using a large molar excess of Eu to the binding sites on the sorbent material at L/S ratio of 10000 mL/g.

Results and Discussion

Materials Tested

DiPhos, PropPhos, and the styrene derivative of IDAA materials were selected for this study, due to promising initial results. Phosphonic acids have been shown to be excellent chelators for REEs, and iminodiacetic acid groups, a close relative of EDTA, have been extensively used for chelation. Base silica materials, either Cab-o-sil (NF Silica) or MCM-41 (NP Silica), were functionalized with DiPhos, PropPhos, or Styrene IDAA in previously optimized methods. In order to determine the increase in performance due to the addition of the ligands, the silica base materials were also tested. We also compared these materials to commercially available sorbents, Chelex100 and activated carbon. Chelex 100 is a commercially available resin that is functionalized with EDTA. Activated carbon is a very common and cheap sorbent but it lacks affinity and selectivity.

It should be noted that the morphology of the sorbent impacts the form factor for end use. For instance, nanofiber silica can be dispersed into Nafion, a porous polymer, resulting in water permeable films that can be used for trace capture. Nanoparticle silica with well-defined channels like MCM-41, work well in packed filter cartridges that waters flow through. For this reason, we used both nanofiber silica and nanoparticle silica as the ligands can be imparted on either substrate interchangeably. Nanoparticle silica has a higher surface area compared to nanofiber silica, since the nanoparticle silica used is mesoporous with pores ranging from 3 to 5 nm in diameter. The nanofiber silica used is not porous, and the particle sizes vary widely. Surface area impacts capacity per gram as more surface area per gram allows for more active sites per gram. Surface area decreases as ligands are added, due to increasing particle size or pore constriction with nanofiber or nanoporous silica respectively (Table 5.1).

TABLE 5

Material surface area and morphology. NF silica is Cab-o-sil EH-5. NP silica is MCM-41. Surface area was measured by BET.

| Material | Surface Area ($m^2/g$) | Particle Size ($\mu m$) |
|---|---|---|
| DiPhos-NF Silica | 123 | 0.2-0.3 |
| PropPhos-NP Silica | 364 | variable |
| IDAA Styrene-NF Silica | 89 | 0.2-0.3 |
| NF Silica | 307 | 0.2-0.3 |
| NP Silica | 551 | variable |
| Chelex 100 Resin | 3 | 75-150 |
| Activated Carbon | 1400 | 150 |

Sorbent Performance in Natural Waters

We tested material performance in a variety of water matrices. The water matrix has a large impact on material performance Real water samples contain many dissolved species, and the ionic strength of water samples can vary by orders of magnitude. River water has the lowest ionic strength, which typically gives the best performance for this class of sorbents. Seawater has a much higher ionic strength, about 700 times that of river water, and for most sorbents this has a huge impact on performance Acidic waters, both those with hydrochloric acid (0.01 M) and nitric acid (0.01 M), were used to model mining waters. Typically, metal capture from acidic solutions is significantly more challenging. Most materials followed the trend of performing best in river water, then seawater, followed by acidic solutions (Table 6).

The percent sorption of all materials tested in natural waters can be found in Table 6. All organic functionalized materials outperformed commercial resins in river water and seawater. DiPhos-NF silica and PropPhos both had outstanding performance, with the base silica controls having almost no affinity for any metals tested. The DiPhos-NF silica removed almost all metals tested from seawater, and maintained high affinity for the tested metals even in acidic solutions; other materials tested lost almost all affinities for REEs in acidic conditions. Activated carbon showed slight uptake with seawater and removed almost half of most metals in river water, significantly underperforming when compared to the functionalized sorbents. Chelex 100 performed poorly in all solutions.

TABLE 6

| Material | Solution | % Sorption | | | | | | | | |
|---|---|---|---|---|---|---|---|---|---|---|
| | | La | Ce | Nd | Eu | Gd | Tb | Dy | Ho | Lu |
| Organic Ligands Modified Sorbent | | | | | | | | | | |
| Diphos-NF Silica | River water | 90 | 89 | 57 | 90 | 89 | 90 | 89 | 90 | 90 |
| | Seawater | 96 | 98 | 98 | 99 | 99 | 99 | 99 | 99 | 99 |
| | $HNO_3$ | 51 | 70 | 79 | 87 | 85 | 87 | 86 | 86 | 94 |
| | HCl | 65 | 80 | 90 | 92 | 90 | 91 | 90 | 91 | 96 |
| PropPhos-NP Silica | River water | 89 | 90 | 80 | 91 | 87 | 92 | 86 | 94 | 97 |
| | Seawater | 65 | 79 | 83 | 91 | 90 | 92 | 95 | 95 | 98 |
| | $HNO_3$ | 6 | 7 | 0 | 7 | 0 | 7 | 0 | 10 | 65 |
| | HCl | 0 | 0 | 13 | 10 | 8 | 10 | 12 | 13 | 75 |
| IDAA Styrene-NF Silica | River water | 82 | 82 | 48 | 81 | 79 | 82 | 79 | 82 | 81 |
| | Seawater | 29 | 47 | 56 | 65 | 58 | 63 | 65 | 64 | 73 |
| | $HNO_3$ | 5 | 5 | 1 | 4 | 4 | 4 | 4 | 4 | 5 |
| | HCl | 0 | 0 | 16 | 4 | 3 | 4 | 4 | 4 | 5 |

TABLE 6-continued

|  |  | % Sorption | | | | | | | | |
|---|---|---|---|---|---|---|---|---|---|---|
| Material | Solution | La | Ce | Nd | Eu | Gd | Tb | Dy | Ho | Lu |
| Support Material | | | | | | | | | | |
| NF Silica | River water | 0 | 0 | 1 | 0 | 0 | 0 | 0 | 0 | 0 |
|  | Seawater | 0 | 0 | 0 | 0 | 0 | 0 | 0 | 0 | 0 |
|  | HNO$_3$ | 4 | 4 | 0 | 4 | 3 | 5 | 4 | 4 | 4 |
|  | HCl | 0 | 0 | 15 | 2 | 1 | 2 | 2 | 2 | 2 |
| NP Silica | River water | 0 | 0 | 0 | 1 | 0 | 0 | 1 | 0 | 9 |
|  | Seawater | 1 | 9 | 11 | 19 | 13 | 16 | 16 | 13 | 14 |
|  | HNO$_3$ | 5 | 5 | 4 | 5 | 4 | 5 | 6 | 5 | 6 |
|  | HCl | 0 | 0 | 10 | 3 | 2 | 3 | 3 | 3 | 2 |
| Commercial Sorbent | | | | | | | | | | |
| EDTA | River water | 0 | 0 | 0 | 0 | 0 | 0 | 0 | 0 | 0 |
| Chelating Resin | Seawater | 0 | 0 | 2 | 9 | 6 | 7 | 7 | 5 | 5 |
| (Chelex 100) | HNO$_3$ | 5 | 5 | 0 | 6 | 6 | 6 | 5 | 7 | 6 |
|  | HCl | 0 | 0 | 14 | 5 | 3 | 5 | 5 | 4 | 4 |
| Activated | River water | 34 | 41 | 23 | 49 | 45 | 49 | 47 | 47 | 47 |
| Carbon (Darco, | Seawater | 0 | 12 | 0 | 25 | 20 | 24 | 23 | 22 | 25 |
| KB-B) | HNO$_3$ | 5 | 4 | 0 | 5 | 0 | 1 | 0 | 5 | 6 |
|  | HCl | 0 | 0 | 14 | 3 | 2 | 3 | 4 | 3 | 2 |

Average of triplicate data and general error <±5%, L/S = 50,000 (mL/g-sorbent), equilibrium pH of river water and seawater were around 5.9 and 6.2, respectively. Concentration of HNO$_3$ and HCl were 0.01M.

This is likely due to the very high liquid to solid ratio, 50,000 mL/g sorbent (this ratio meant that we had 0.1 mg of sorbent per five mL of solution tested). When taking sorbents into real life applications, such as handling thousands of gallons of water per minute, they must perform at very high liquid to solid ratios. The ability of DiPhos-NF silica to perform at these high volumes of water, as well as function efficiently in competitive and acidic environments, has proven that this material is an excellent option for the removal of REEs from a variety of aqueous solutions.

5.3.3 Sorbent Kinetics in River Water

Figure 4:
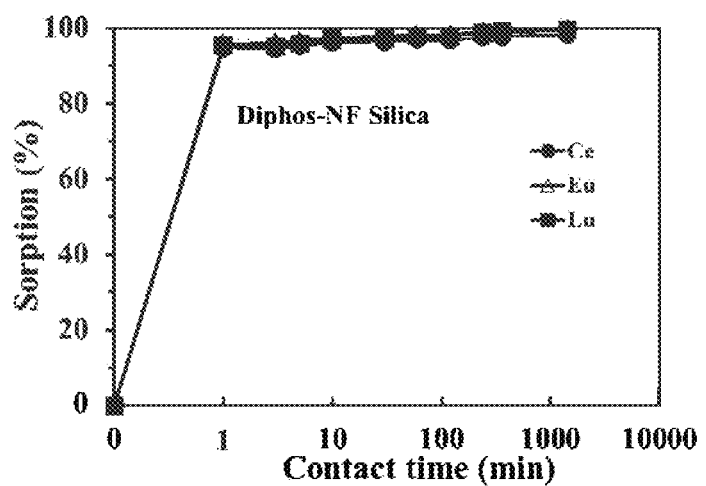
FIG. 4. Diphos-NF Sorption kinetics. In seawater at conditions of pH ~5.9, initial concentration of Eu ~65 ppb, and L/S=50000 mL/g-sorbent.
Figure 5:
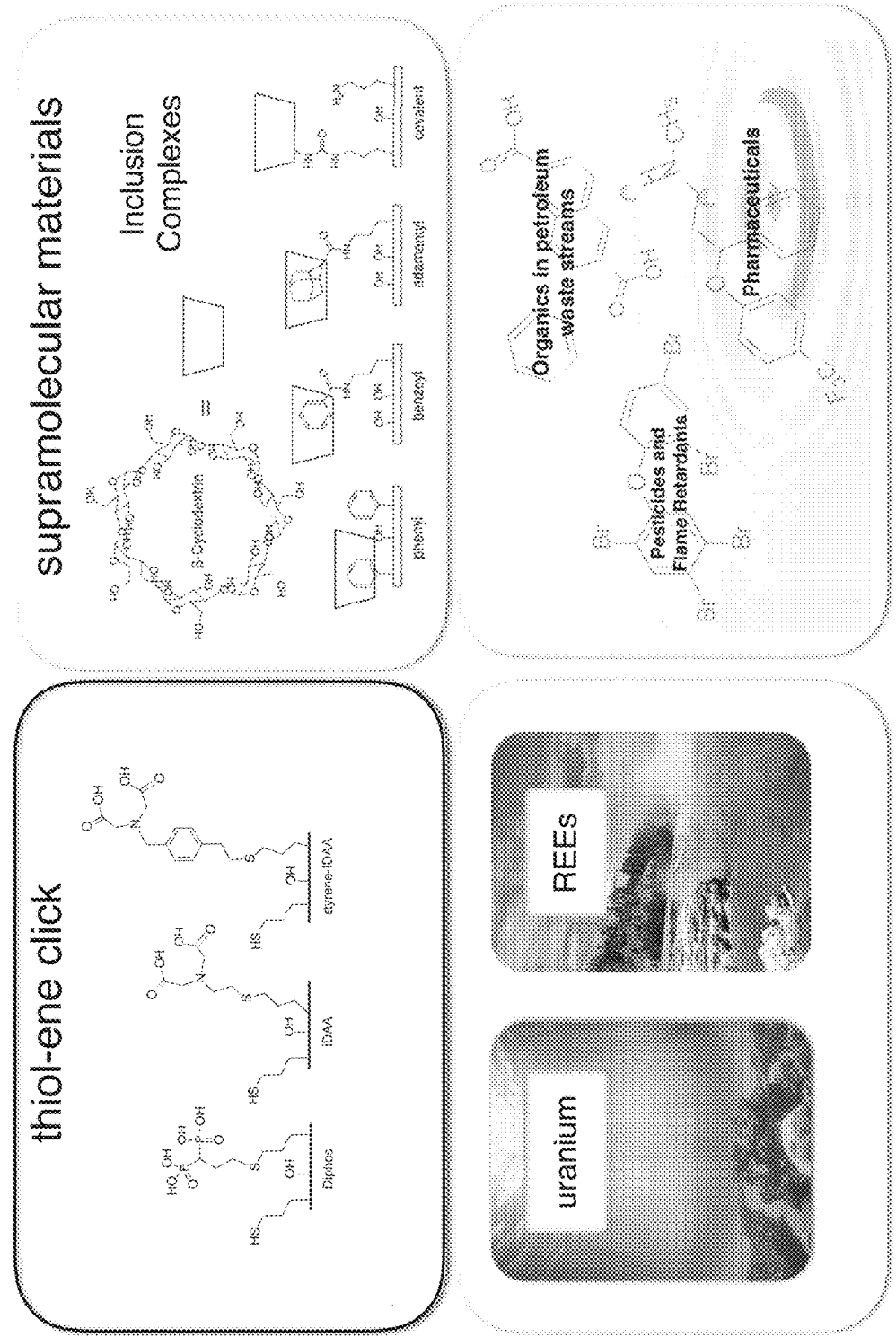
FIG. 5. Illustrative ligands and target species.
Figure 6:
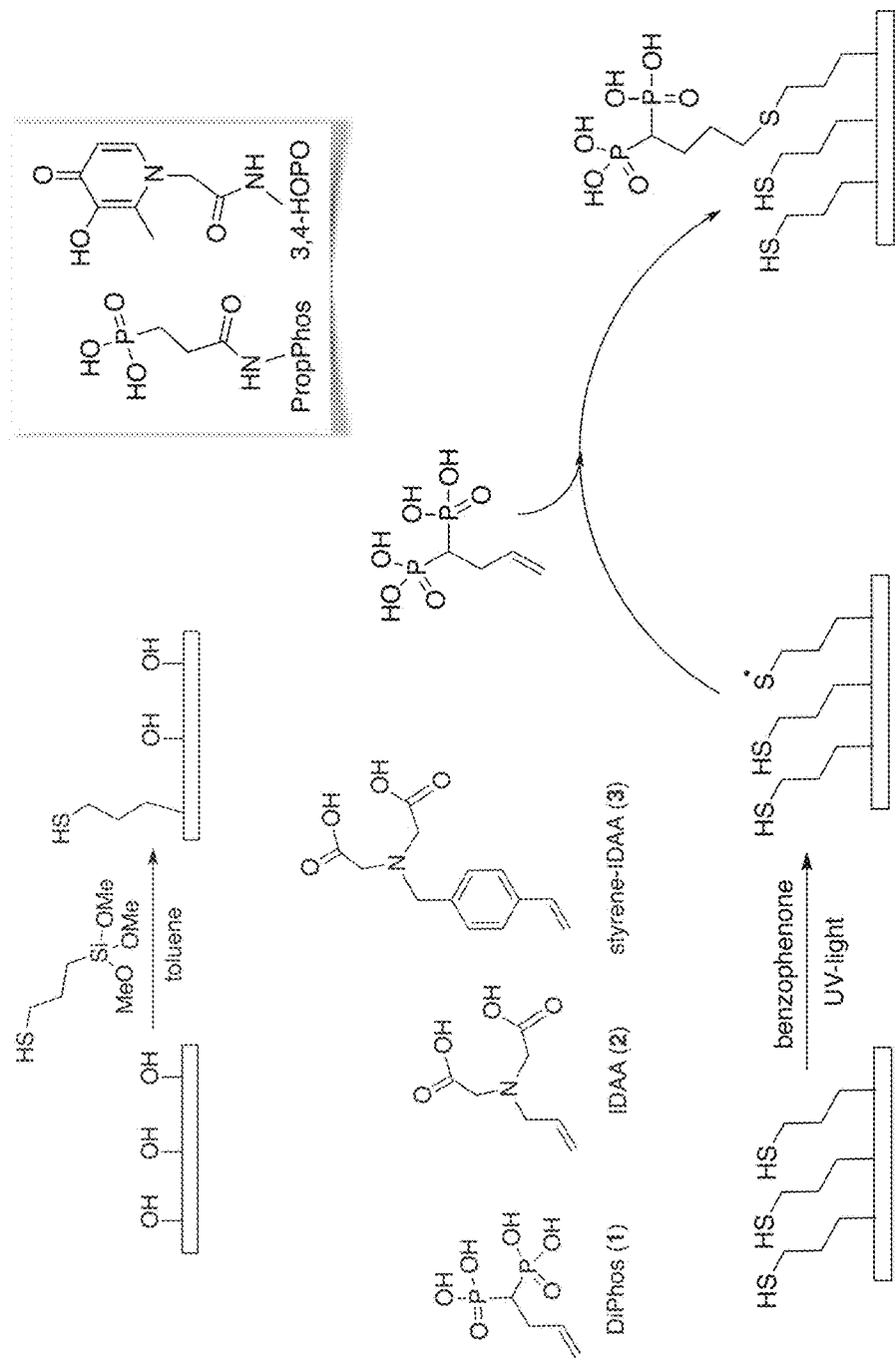
FIG. 6. Scheme for thiol-ene surface functionalization. The silica surface is denoted with a box, this represents any of the silica materials functionalized with mercaptopropyl groups.
Figure 7:
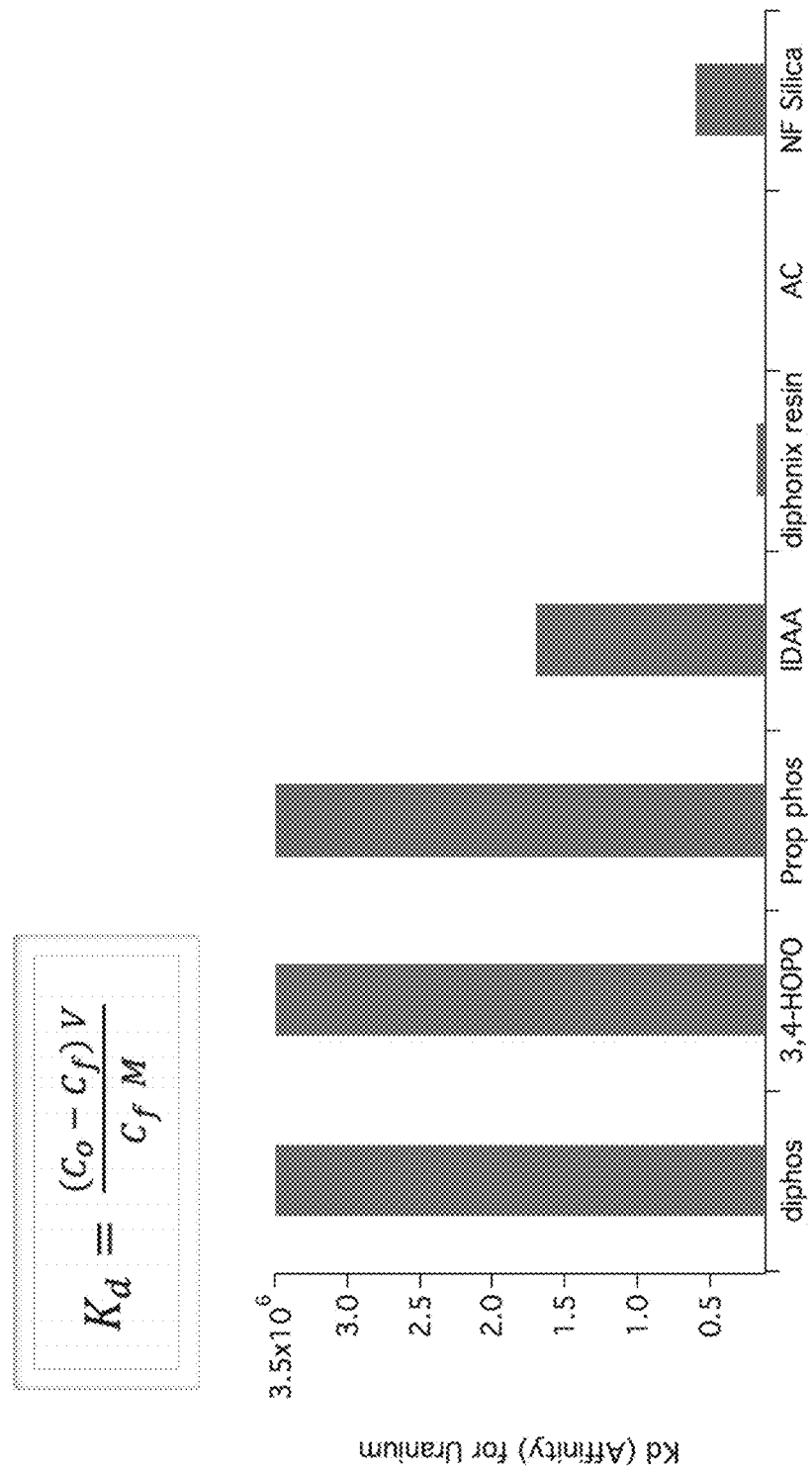
FIG. 7 is graph showing affinity of sorbent materials for uranium.
Figure 8:
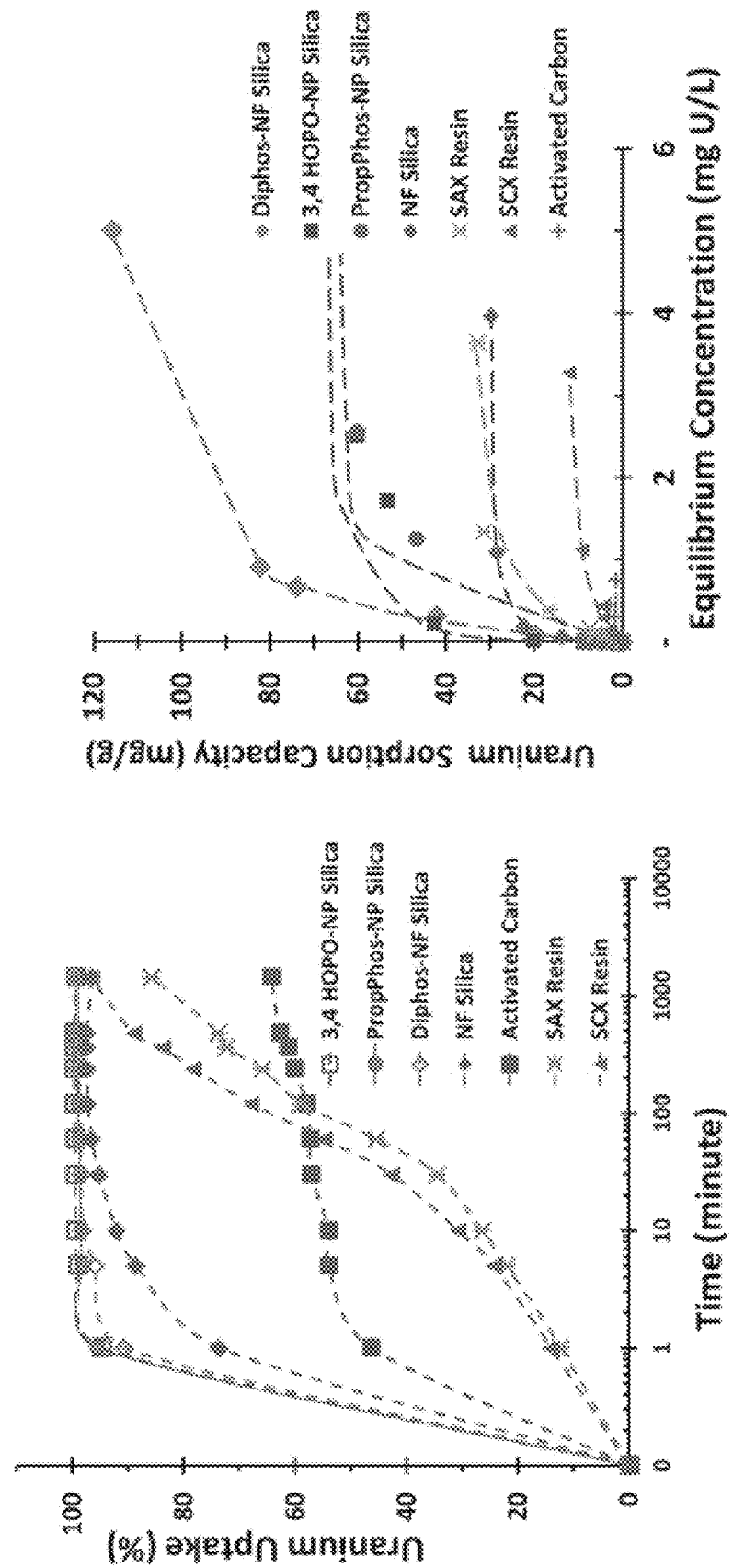
FIG. 8 are graphs showing kinetics and capacity of sorbent materials.
Figure 9:
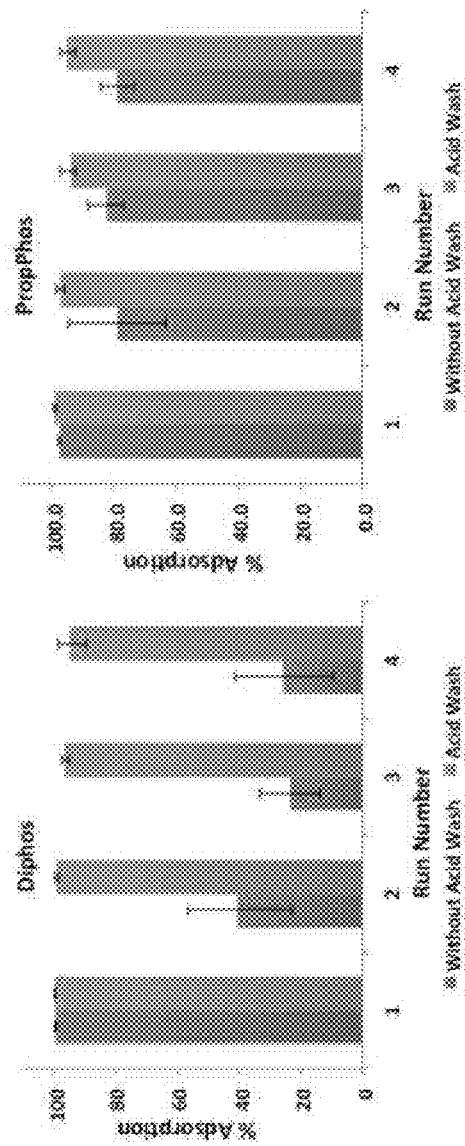
FIG. 9 are graphs showing regeneration of sorbent materials.
Figure 9:
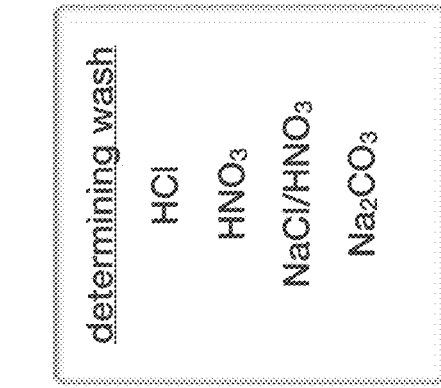
Figure 10:
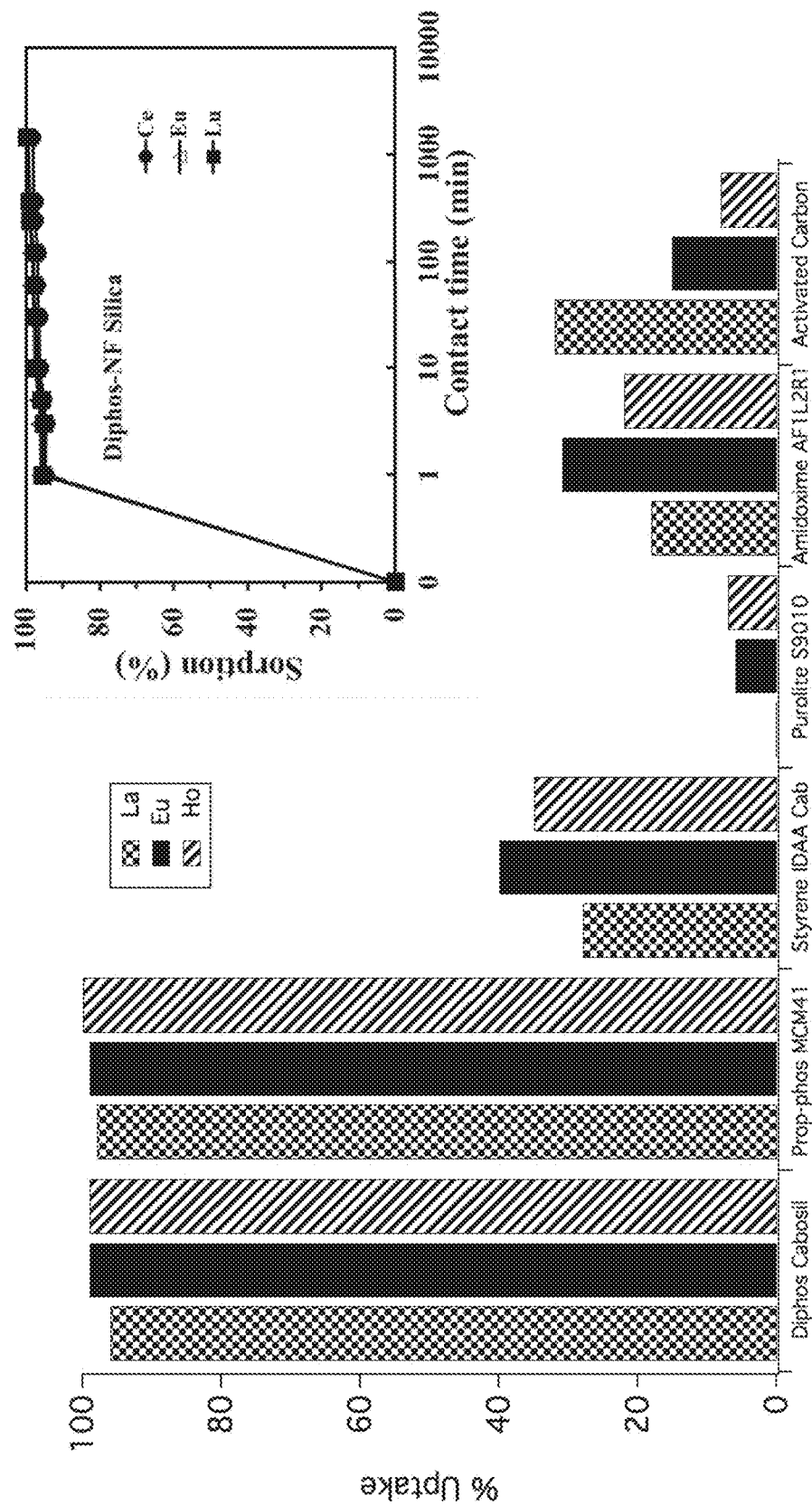
FIG. 10 is a graph showing performance of sorbent materials in geothermal brines.
Figure 11:
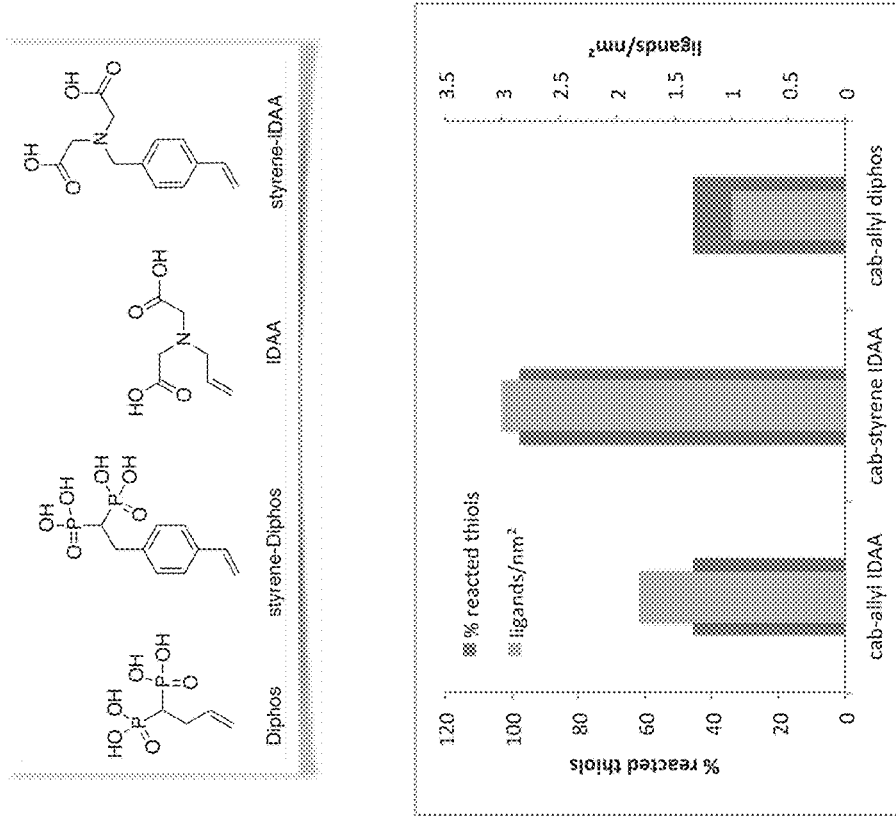
FIG. 11 are graphs showing loading of ligands.
Figure 12:
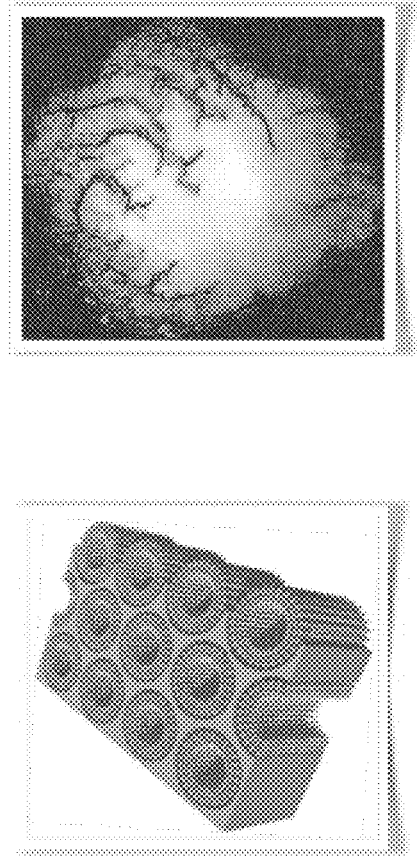
FIG. 12 shows several different support materials.

The functionalized sorbents show excellent removal for a variety of REEs; it is important to note how quickly this removal can take place. In practice, the material would be stripped of metals after equilibrium has been reached and reused. If it took an hour to reach equilibrium, one could collect 24 batches of REEs per day. Following this, if it takes one minute, the process could cycle 1,440 times per day. The kinetics of uptake significantly impacts the economic feasibility of REE recovery from aqueous systems. For DiPhos-NF, equilibrium is reached almost immediately; after only one minute. At this point, over 95% of each metal tested was bound (FIG. 4). The commercial sorbents tested varied for each REE tested. Lutetium had the highest rate of uptake and reached equilibrium 10 times slower than DiPhos, taking ten minutes. The materials had the lowest affinity for cerium; reaching equilibrium after 100 minutes with only 60% of the metal bound. Clearly, the DiPhos-NF silica displayed excellent performance, in terms of both kinetic and percent sorption for all three REEs tested.

Sorbent Capacity

Along with removal and kinetics, capacity is an important metric for determining the feasibility of using these materials for aqueous REE capture in a commercial plant. Capacity is a measure of the amount of the desired analyte that the material is able to taken up, typically measured in mg analyte per gram sorbent material. The higher this number is the higher the quantity of REEs that will be collected in each run. It should be noted that the capacity is dependent on the concentration in solution.

To determine the sorption capacities of materials, adsorption isotherms were determined for selected sorbent materials in river water. The Langmuir model was used to fit the experiment data and explain the sorption capacities of materials. The estimated parameters of the Langmuir isotherm for all sorbents are given in Table 5.6, and were calculated using Equation 3 below, where $C_e$ the equilibrium concentration of Eu in the solution, q is the amount of Eu adsorbed on the unit mass of sorbent, $q_{max}$ is the Eu adsorbed at saturation and represents the maximum capacity of sorbent for metal adsorption, b is the Langmuir constant defined as the adsorption affinity of the sorbent for the metal.

$$\frac{C_e}{q_e} = \frac{1}{q_{max}b} + \frac{C_e}{q_{max}} \quad (3)$$

The sorption isotherm data of both sorbents tested fit the Langmuir adsorption model with $R^2 > 0.98$ (Table 7). This indicates that the adsorption properties correlate almost perfectly with the Langmuir equation, suggesting that the europium interacts with binding sites in a monolayer adsorption behavior with no interaction between Eu ions.

DiPhos-NF had a significantly increased capacity over activated carbon, even though activated carbon has more than ten times the surface area. The capacity is so high in the DiPhos-NF material due to the much greater affinity afforded by the surface ligands, as seen in the value of b. The DiPhos material is able to collect over four times more REEs than the activated carbon, and activated carbon required increasing the concentration of europium almost tenfold to reach capacity. Because of this, it is very unlikely that activated carbon would reach capacity in environmentally relevant concentrations.

TABLE 7

Estimated parameters of the Langmuir isotherm model for Eu sorption on functionalized and commercial and sorbents. $q_{max}$ is the Eu adsorbed at saturation and represents the maximum capacity of sorbent for metal adsorption, b is the Langmuir constant defined as the adsorption affinity of the sorbent for the metal.

| Material | qmax (mg/g sorbent) | b (L/mg) | $R^2$ |
|---|---|---|---|
| DiPhos-NF Silica | 95.24 | 21.00 | 0.9993 |
| Activated Carbon | 22.12 | 3.27 | 0.9988 |

Sorbent Performance in Geothermal Waters

The sorption capacity varies with concentration of REEs found in solution. In order to improve the economic return on collecting REE from aqueous solutions, we need to target the most concentrated aqueous solutions. Some of these aqueous solutions are mining waste streams which are acidic in nature and the performance of our materials in these simulated solutions can be seen above (Table 6). Other natural water sources with elevated concentrations of REEs include geothermal waters.

The dissolved metals in geothermal waters are strongly dependent on site specific mineral deposits, but in some locations, the concentrations can be in high enough ppb ranges that collection of significant metals is possible and profitable. It is also advantageous that the DiPhos-NF silica materials tested remove almost all soft precious metals from solutions, allowing for tandem collection of REEs and precious metals. In order to determine the economic feasibility of removing dissolved metals, we had to ensure that desired metals were present in the locations of interest. Concentrations of respective metals are shown in Table 8, along with the market price. It is evident that the price of precious metals like gold and platinum are significantly higher than the REEs that are present.

TABLE 8

Brine mineral concentrations from selected average geothermal sites and the mineral concentrations documented from Salton Sea. Selected averages are samplings from Idaho Batholith.

| Element | Selected Average | | Salton Sea | | Market Price* |
|---|---|---|---|---|---|
| Cerium | 1553 | ng/L | 367 | ng/L | $0.96/lb |
| Copper | 0.29 | mg/kg | 1 | mg/kg | $3/lb |
| Dysprosium | 60 | ng/L | 55 | ng/L | $103/lb |
| Erbium | 26 | ng/L | 34 | ng/L | $32/lb |
| Europium | 16 | ng/L | 55 | ng/L | $93/lb |
| Gadolinium | 86 | ng/L | 14 | ng/L | $9/lb |
| Gold | 17 | µg/kg | 100 | µg/kg | $1,250/troy ounce |
| Holmium | 10 | ng/L | 11 | ng/L | $25/lb |
| Lanthanum | 672 | ng/L | 305 | ng/L | $0.96/lb |
| Lutetium | 0 | ng/L | 7 | ng/L | $498.95/lb |
| Manganese | 499 | mg/kg | 500 | mg/kg | $0.74/lb |
| Neodymium | 660 | ng/L | 77 | ng/L | $18.10/lb |
| Palladium | 11 | µg/kg | 11 | µg/kg | $750/troy ounce |
| Platinum | 19 | µg/kg | 100 | µg/kg | $1,325/troy ounce |
| Praseodymium | 133 | ng/L | 700 | ng/L | $25/lb |
| Samarium | 86 | ng/L | 305 | ng/L | $1.18/lb |
| Silver | 259 | µg/kg | 600 | µg/kg | $20/troy ounce |
| Terbium | 11 | ng/L | 12 | ng/L | $204.12/lb |
| Thulium | 0 | ng/L | 5 | ng/L | $453.59/lb |
| Ytterbium | 23 | ng/L | 40 | ng/L | $22.68/lb |
| Zinc Zn | 307 | mg/kg | 180 | mg/kg | $0.70/lb |

*Pricing available from: Argus Media Ltd. (UK), Stormcrow Capital Ltd. (Canada)

Geothermal waters have even more dissolved ions than seawater (ionic strength varies based on location); to ensure that the materials were capable of removing REEs from this very competitive environment, we tested them in water collected from a hot spring (Table 9). It should be noted that performance experiments were run at room temperature, so conditions were not identical to what would be seen in a collection facility that drew directly from geothermal waters. In geothermal waters at room temperature, both Diphos-NF Silica and PropPhos-NP Silica had outstanding performance, nearing perfection with almost 100% sorption for each ion after two hours. The IDAA materials underperformed in the elevated ionic strength, but still outperformed the commercial sorbents tested (Table 9).

TABLE 9

Material performance testing in geothermal waters. Equilibrium pH ~7.7, L/S 50,000, 2 hours for contact time.

| Material | La | Eu | Ho |
|---|---|---|---|
| Organic ligands Modified Sorbent | | | |
| Diphos-NF Silica | 96 | 99 | 99 |
| PropPhos-NP Silica | 98 | 99 | 100 |
| IDAA Styrene-NF Silica | 28 | 40 | 35 |
| Support Material | | | |
| NF Silica | 7 | 22 | 23 |
| NP Silica | 0 | 29 | 48 |
| Commercial Sorbent | | | |
| EDTA Chelating Resin (Chelex 100) | 1 | 2 | 3 |
| Activated carbon (Darco, KB-B) | 32 | 15 | 8 |

The demand for rare earth elements is rising, and because REEs are produced almost entirely in China, this market control can lead to fluctuating prices and inconsistency in availability. There are trace concentrations of REEs found in most natural waters, with the concentration present in each being location and water specific. For instance, geothermal waters contain on average more dissolved REEs than surface water, with some geothermal waters having concentrations upwards of 100 ppb. Trace collection of these metals from geothermal waters may provide a new source for REEs.

Selective sorbent materials can be excellent for trace collection. We were looking for three main parameters for an ideal sorbent: the sorbent has to remove almost all REEs present in waters with high ionic strengths, collection had to happen quickly, and the materials had to have a high capacity that did not require high concentrations to reach. DiPhos-NF silica met all desired criteria, removing 99% of REEs even in geothermal waters (highest ionic strength), % sorbtion reached 95% in under a minute, and the capacity was significantly higher than with any commercial sorbents.

Disclosed herein materials for trace collection of REEs from natural waters. The rate of uptake would allow for collection and recycling of materials to happen in mere minutes, for upwards of 1,000 collection cycles per day. These materials were tested in even the most competitive of solutions, geothermal waters, and were still found to have outstanding performance. These materials may be part of the solution to decrease the dependence on China for REEs needed for alternative energy and technology.

In view of the many possible embodiments to which the principles of the disclosed materials may be applied, it should be recognized that the illustrated embodiments are only preferred examples of the invention and should not be taken as limiting the scope of the invention.

What is claimed is:

1. A material comprising:

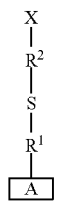

wherein A is a solid support surface; $R^1$ is $(\text{---CH}_2\text{---})_n$; $R^2$ is $(\text{---CH}_2\text{---})_m$ or $(\text{---CH}_2\text{---})_a\text{Ph}(\text{---CH}_2\text{---})_b$; X is selected from $\text{---CH(P(=O)(OH)}_2)_2$, or $\text{---N(---CH}_2\text{---COOH)}_2$; and n is 1 to 6; m is 2 to 6; a is 2 to 6; and b is 1 to 6; wherein Ph is a phenylene.

2. The material of claim 1, further comprising a hydroxy or a thioalkyl directly bound to A.

3. The material of claim 1, wherein n is 3.

4. The material of claim 1, wherein $R^2$ is $(\text{---CH}_2\text{---})_m$ and m is 3.

5. The material of claim 1, wherein $R^2$ is $(\text{---CH}_2\text{---})_a\text{Ph}(\text{---CH}_2\text{---})_b$.

6. The material of claim 1, wherein $R^2$ is $(\text{---CH}_2\text{---})_a\text{Ph}(\text{---CH}_2\text{---})_b$ and a is 2 and b is 1.

7. The material of claim 3, wherein X comprises a phosphonic acid moiety or an iminodiacetic acid moiety.

8. The material of claim 1, wherein A comprises a silica substrate.

9. A material comprising a functionalized solid support surface, wherein the functionalization comprises a thioalkylene linker bound to the support surface and the thioalkylene linker is coupled to a moiety derived from a ligand, wherein the ligand includes a terminal alkenyl and at least one first functional group configured to bind to at least one predetermined target species, and wherein the solid support surface comprises a silica substrate, and wherein the first functional group comprises a phosphonic acid moiety or an iminodiacetic acid moiety.

10. The material of claim 9, further comprising at least one second functional group bound to the support surface and configured to bind to at least one predetermined target species, wherein the at least one second functional group is selected from a thioalkyl or a hydroxy.

11. The material of claim 9, wherein the target species are selected from a metal, a metalloid, an oxyanion, a radioactive species, a polar organic compound, or a combination thereof.

12. A method for capturing at least one target species from an aqueous source comprising contacting the aqueous source containing at least one target species with the material of claim 1 and capturing the at least one species onto the material of claim 1.

13. A method for capturing at least one target species from an aqueous source comprising contacting the aqueous source containing at least one target species with the material of claim 12 and capturing the at least one species onto the material of claim 12.

14. The method of claim 12, wherein the target species are selected from a metal, a metalloid, an oxyanion, a radioactive species, a polar organic compound, or a combination thereof.

15. The method of claim 13, wherein the target species are selected from a metal, a metalloid, an oxyanion, a radioactive species, a polar organic compound, or a combination thereof.

16. The method of claim 12, wherein the target species is selected from arsenic, selenium, cobalt, silver, cadmium, mercury, thallium, lead, uranium, rare earth element, copper or zinc.

17. A material comprising:

wherein A is a solid support surface; $R^1$ is $(13\ \text{CH}_2\text{---})_n$; $R^2$ is $(\text{---CH}_2\text{---})_m$ or $(\text{---CH}_2\text{---})_a\text{Ph}(\text{---CH}_2\text{---})_b$; X comprises a phosphonic acid moiety or an iminodiacetic acid moiety; and n is 1 to 6; m is 2 to 6; a is 2 to 6; and b is 1 to 6; wherein Ph is a phenylene.

18. A material comprising:

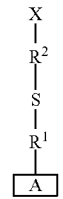

wherein A is a solid support surface; $R^1$ is $(\text{---CH}_2\text{---})_n$; $R^2$ is $(\text{---CH}_2\text{---})_m$ or $(\text{---CH}_2\text{---})_a\text{Ph}(\text{---CH}_2\text{---})_b$; X is a urea, thiourea, phosphinimine, hydroxypyridinoate (HOPO), sulfocatecholamide (CAMS), terephthalimide, carbamoylmethylphosphine oxide (CMPO), phosphine derivative, phosphine oxide derivative, sulfonamide derivative, ethylenediaminetetraacetic acid (EDTA) derivative, dihydroxybenzene, or N-phenyliminodiacetic acid; and n is 1 to 6; m is 2 to 6; a is 2 to 6; and b is 1 to 6; wherein Ph is a phenylene.

19. A material comprising:

wherein A is a solid support surface; $R^1$ is $(\text{---CH}_2\text{---})_n$; $R^2$ is $(\text{---CH}_2\text{---})_a\text{Ph}(\text{---CH}_2\text{---})$b; X is a first functional group configured to bind to at least one predetermined target species; and n is 1 to 6; a is 2 to 6; and b is 1 to 6; wherein Ph is a phenylene.

20. A material comprising a functionalized solid support surface, wherein the functionalization comprises a thioalkylene linker bound to the support surface and the thioalkylene linker is coupled to a moiety derived from a ligand, wherein the ligand includes a terminal alkenyl and at least one first functional group configured to bind to at least one predetermined target species, and wherein the solid support surface comprises a silica substrate, and wherein the first functional group is selected from —N(CH$_2$CO$_2$H)$_2$, —NHCONH$_2$, —NHCSNH$_2$, —SO$_2$NH$_2$, or —NHCOCH$_2$P(=O)R'R") wherein R' and R" are independently lower alkyl or aryl groups.

* * * * *